US009937107B2

(12) United States Patent
Hokii et al.

(10) Patent No.: US 9,937,107 B2
(45) Date of Patent: Apr. 10, 2018

(54) FLUOROALUMINOSILICATE GLASS POWDER

(71) Applicant: GC CORPORATION, Tokyo (JP)

(72) Inventors: Yusuke Hokii, Tokyo (JP); Ryosuke Yoshimitsu, Tokyo (JP); Shoichi Fukushima, Tokyo (JP); Futoshi Fusejima, Tokyo (JP)

(73) Assignee: GC CORPORATION, Tokyo (JP)

( * ) Notice: Subject to any disclaimer, the term of this patent is extended or adjusted under 35 U.S.C. 154(b) by 0 days.

(21) Appl. No.: 15/318,873

(22) PCT Filed: Jun. 24, 2015

(86) PCT No.: PCT/JP2015/068217
§ 371 (c)(1),
(2) Date: Dec. 14, 2016

(87) PCT Pub. No.: WO2016/002600
PCT Pub. Date: Jan. 7, 2016

(65) Prior Publication Data
US 2017/0143593 A1 May 25, 2017

(30) Foreign Application Priority Data
Jun. 30, 2014 (JP) ................................. 2014-134820

(51) Int. Cl.
A61K 6/083 (2006.01)
C03C 12/00 (2006.01)
C04B 28/34 (2006.01)
A61K 6/00 (2006.01)
A61K 6/027 (2006.01)
C04B 111/00 (2006.01)

(52) U.S. Cl.
CPC .......... A61K 6/0835 (2013.01); A61K 6/0005 (2013.01); A61K 6/0276 (2013.01); C03C 12/00 (2013.01); C04B 28/344 (2013.01); C04B 2111/00836 (2013.01)

(58) Field of Classification Search
None
See application file for complete search history.

(56) References Cited

U.S. PATENT DOCUMENTS

| 5,520,725 A * | 5/1996 | Kato ................... A61K 6/0023 106/35 |
| 6,280,863 B1* | 8/2001 | Frank ................... C03C 4/0021 106/35 |
| 8,168,693 B2* | 5/2012 | Ritter .................. A61K 6/0005 106/35 |
| 2005/0054509 A1* | 3/2005 | Hoen ................... A61K 6/033 501/10 |
| 2005/0209082 A1 | 9/2005 | Apel et al. |
| 2006/0205582 A1* | 9/2006 | van't Hoen ............ A61K 6/033 501/8 |
| 2011/0218268 A1* | 9/2011 | Ritter .................. A61K 6/0005 523/117 |
| 2012/0135059 A1 | 5/2012 | Tsunekawa et al. |
| 2014/0090580 A1* | 4/2014 | Hokii ................... A61K 6/025 106/462 |

FOREIGN PATENT DOCUMENTS

| CA | 2239861 A1 | 12/1998 |
| CA | 2239865 A1 | 12/1998 |
| GB | 2495587 A | 4/2013 |
| JP | 1129342 A | 2/1999 |
| JP | 2005-075724 A | 3/2005 |
| JP | 2007-269675 A | 10/2007 |
| JP | 2011-162435 A | 8/2011 |
| JP | 2013-087054 A | 5/2013 |
| JP | 2014-070047 A | 4/2014 |

OTHER PUBLICATIONS

International Search Report dated Oct. 6, 2015; PCT/JP2015/068217.

* cited by examiner

Primary Examiner — Peter A Salamon
(74) Attorney, Agent, or Firm — Ladas & Parry LLP

(57) ABSTRACT

Provided is a fluoroaluminosilicate glass powder that can provide a dental glass ionomer cement hardened body excellent in acid resistance, the glass powder including sodium and potassium which have an effect of lowering the reflective index of glass. A mass ratio of potassium to sodium in the component is in the range of from 1.2 to 1.9 in terms of oxide.

12 Claims, No Drawings

FLUOROALUMINOSILICATE GLASS POWDER

TECHNICAL FIELD

The present invention relates to fluoroaluminosilicate glass powder that can be suitably used for dental glass ionomer cement compositions.

BACKGROUND ART

In using a dental glass ionomer cement, a polymer acid including an acid such as polycarboxylic acid as the main component and a glass powder for glass ionomer cements are allowed to react to each other under the presence of water, and hardened. This kind of glass ionomer cement has excellent characteristics, for example very good biocompatibility, excellent aesthetic property of semi-transparent hardened body, excellent adhesion to tooth substrates such as enamel and dentine, and when the glass powder includes fluoride, it has anticariogenic effect by the fluoride. Thus, the glass ionomer cement is widely used in dentistry, for example for filling cavities of dental caries, for cementing crowns, inlays, bridges and orthotic bands, for cavity linings, sealers for filling root canals, abutment construction, preventive sealings, and so on.

In order to improve the characteristics of the dental glass ionomer cement hardened body, such as the transparency and acid resistance, glass powders for glass ionomer cements to be blended in dental glass ionomer cement compositions have been developed. For example, the applicant of the present invention developed a glass powder for a dental glass ionomer cement, having a specific composition including Na and K which have an effect of lowering the refractive index of glass, and having a refraction index nd of 1.42 to 1.47 (see Patent Literature 1 for example). The refractive index nd of the glass powder is 1.42 to 1.47, which is lower than that of conventional glass powders, and the difference from the refractive index nd (approximately 1.42) of the matrix component of a practically useful dental glass ionomer cement is small. Thus, the glass powder can provide a hardened body with a high transparency. However, the glass powder tends to lower the acid resistance of the hardened body by including Na and K. In this point, the glass powder has a room for improvement.

The applicant of the present invention also developed a fluoroaluminosilicate glass powder in which a lanthanum compound, which is dissolved in the presence of polycarboxylic acid and water, exists only on the surface layers of the powder particles, for the purpose of improving the acid resistance of dental glass ionomer cement (see Patent Literature 2 for example). However, adjustment of the hardening speed of cement is also important for the dental glass ionomer cement, and as the method for adjusting the speed, generally carried out are treatments on the surface of the fluoroaluminosilicate glass powder by acid and the like. The technique of Patent Literature 2 carries out a treatment on the surface of the fluorialuminosilicate glass powder, therefore has a problem of difficulty in satisfying both of the treatment and the method for adjusting the hardening speed of the cement.

CITATION LIST

Patent Literatures

Patent Literature 1: JP 2007-269675 A
Patent Literature 2: JP 2014-070047 A

SUMMARY

Technical Problem

An object of the present invention is to provide a fluoroaluminosilicate glass powder with which a dental glass ionomer cement hardened body excellent in acid resistance can be obtained, the hardened body including sodium and potassium which have an effect of lowering the refractive index of glass.

Solution to Problem

As a result of intensive researches for solving the above problem, the inventors of the present invention found that a fluoroaluminosilicate glass powder having a specific range of mass ratio of potassium to sodium in the component has a good acid resistance and can provide a high transparency to a dental glass ionomer cement hardened body to be obtained by the effect of sodium and potassium of lowering the refractive index of grass.

The present invention is a fluoroaluminosilicate glass powder wherein a mass ratio of potassium to sodium in component is in the range of from 1.2 to 1.9 in terms of oxide.

Advantageous Effects of Invention

According to the fluoroaluminosilicate glass powder of the present invention, it is possible to obtain a dental glass ionomer cement hardened body excellent in acid resistance, the hardened body including sodium and potassium which have an effect of lowering the refractive index of glass.

DESCRIPTION OF EMBODIMENTS

The fluoroaluminosilicate glass powder according to the present invention includes, as its components, silicon, aluminum, fluorine, sodium and potassium. In the glass, these components exist as oxides, except fluorine which exists as simple substance (ion). That is, silicon exists as silicon dioxide (silica), aluminum exists as aluminum oxide (alumina), sodium exists as sodium oxide, and potassium exists as potassium oxide. Thus, in the present invention, the amount of each component in the glass is shown as the amount of corresponding oxide, except fluorine.

The silicon, aluminum and fluorine included in the fluoroaluminosilicate glass powder according to the present invention form the framework of the fluoroaluminosilicate glass. With this formation, fluorine having an anticariogenic effect is gradually released. Therefore, the glass powder is especially suitable for dental glass ionomer cements.

The content of the silicon in the fluoroaluminosilicate glass powder according to the present invention is preferably in the range of from 15 mass % to 30 mass % in terms of oxide, in view of easy manufacturing. The content is further preferably in the range of from 19 mass % to 26 mass %. The content can be determined by elemental analysis measurements such as ICP and fluorescent X-ray analysis.

The content of the aluminum in the fluoroaluminosilicate glass powder according to the present invention is preferably in the range of from 15 mass % to 30 mass % in terms of oxide, in view of easy manufacturing. The content is further preferably in the range of from 18 mass % to 28 mass %.

The content of the fluorine in the fluoroaluminosilicate glass powder according to the present invention is preferably in the range of from 13 mass % to 40 mass % and further preferably in the range of from 17 mass % to 34 mass %, in view of easy manufacturing.

The sodium and potassium included in the fluoroaluminosilicate glass powder according to the present invention both have an effect of lowering the refractive index of fluoroaluminosilicate glass. The lowering of the refractive index of the glass makes the difference between the refractive index of the glass and the refractive index of the matrix component of the dental glass ionomer cement small, thus the transparency of the dental glass ionomer cement hardened body to be obtained gets high.

The mass ratio of the potassium to the sodium in the fluoroaluminosilicate glass powder according to the present invention is in the range of from 1.2 to 1.9 in terms of oxide. With this range, the dental glass ionomer cement hardened body improves its acid resistance while including sodium and potassium. On the other hand, if the mass ratio is outside the range, the acid resistance tends to degrade. The mass ratio is more preferably in the range of from 1.43 to 1.67, and further preferably in the range of from 1.48 to 1.61.

The content of sodium in the fluoroaluminosilicate glass powder according to the present invention is, in terms of oxide, preferably in the range of from 2 mass % to 6 mass % and further preferably in the range of from 2.4 mass % to 3.3 mass %, in view of easy manufacturing.

The content of potassium in the fluoroaluminosilicate glass powder according to the present invention is, in terms of oxide, preferably in the range of from 3 mass % to 8 mass % and further preferably in the range of from 3.9 mass % to 5.1 mass %, in view of easy manufacturing.

In order to introduce sodium and potassium in the fluoroaluminosilicate glass powder, a method of blending a sodium compound and a potassium compound as raw materials may be given. Examples of the sodium compound include sodium fluoride, sodium chloride, sodium hydroxide, sodium carbonate, disodium hydrogenphosphate, sodium dihydrogenphosphate, sodium metaphosphate, and cryolite. They may be used alone or in combination.

Examples of the potassium compound include potassium fluoride, potassium chloride, potassium carbonate, potassium hydrogencarbonate, dipotassium hydrogenphosphate, potassium dihydrogenphosphate, potassium polyphosphate, and potassium metaphosphate. They may be used alone or in combination.

The fluoroaluminosilicate glass powder according to the present invention may further include a rare earth element or bismuth. By including a rare earth element or bismuth, the acid resistance of the dental glass ionomer cement hardened body further improves. Examples of the rare earth element include scandium, yttrium, lanthanum, cerium, praseodymium, neodymium, promethium, samarium, europium, gadolinium, terbium, dysprosium, holmium, erbium, thulium, ytterbium and lutetium. Among them, yttrium, lanthanum, cerium and ytterbium are especially preferable because they have excellent effect of improving acid resistance. They may be used alone or in combination.

The mass ratio of the rare earth element or bismuth to the sodium in the fluoroaluminosilicate glass powder according to the present invention is preferably in the range of from 0.1 to 1.5 in terms of oxide. If the mass ratio is less than 0.1, it tends to be difficult to obtain the effect of improving acid resistance, and if the mass ratio is more than 1.5, the refraction index of the glass extremely increases and the transparency tends to degrade. The mass ratio is more preferably in the range of from 0.47 to 1.25.

The content of the rare earth element or bismuth in the fluoroaluminosilicate glass powder according to the present invention is, in terms of oxide, preferably in the range of from 0.5 mass % to 10 mass % and further preferably in the range of from 1.4 mass % to 8.4 mass %, in view of easy manufacturing.

In order to introduce a rare earth element or bismuth in the fluoroaluminosilicate glass powder, a method of blending a compound of a rare earth element or bismuth as a raw material may be given. Examples of the compound of a rare earth element or bismuth include oxides, hydroxides, chlorides and fluorides of a rare earth element or bismuth.

The fluoroaluminosilicate glass powder according to the present invention may further include nitrogen, magnesium, calcium, barium, phosphorus, boron, zirconium, tantalum, strontium, and the like.

If phosphorus is included from the above, the content thereof is, in terms of oxide, preferably in the range of from 0.5 mass % to 15 mass % and further preferably in the range of from 1.9 mass % to 8.3 mass %, in view of easy manufacturing.

If strontium is included from the above, the content thereof is, in terms of oxide, preferably in the range of from 2 mass % to 20 mass % and further preferably in the range of from 10 mass % to 17.2 mass %, in view of easy manufacturing.

As a method for manufacturing the fluoroaluminosilicate glass powder according to the present invention, for example a method of: mixing the above-described raw materials in predetermined amounts; melting them at a temperature of no less than 1000° C., preferably in the range of from 1100° C. to 1500° C. and cooling them to obtain a block of fluoroaluminosilicate glass; and thereafter pulverizing the block may be given.

The particle size of the fluoroaluminosilicate glass powder according to the present invention is preferably in the range of from 0.02 μm to 20 μm as the average particle size. If the average particle size is more than 20 μm, it may be rough on the tongue when used as a filling cement, or the abrasion resistance tends to degrade. Meanwhile, if a fine powder having an average particle size of less than 0.02 μm is used, it gets extremely difficult to mix the powder, therefore the operability tends to degrade. It is noted that the average particle size is the average value of the long diameter and the short diameter (long-short mean diameter).

The refraction index $n_d$ of the fluoroaluminosilicate glass powder according to the present invention is preferably in the range of from 1.42 to 1.47. If the refraction index $n_d$ is within this range, it is possible to make the difference with the refractive index $n_d$ (approximately 1.42) of the matrix component of a practically useful dental glass ionomer cement small, and increase the transparency of the dental glass ionomer cement hardened body to be obtained.

Hereinafter the present invention will be more specifically described with Examples and Comparative Examples. However, the present invention is not limited to these Examples.

EXAMPLES

<Manufacture of Fluoroaluminosilicate Glass Powder>

Silica in an amount of 27.5 g, 12.7 g of alumina, 16.7 g of aluminum fluoride, 18.6 g of strontium fluoride, 8.8 g of aluminum phosphate, 4.2 g of sodium fluoride, 5.6 g of potassium fluoride and 5.9 g of lanthanum fluoride were sufficiently mixed in a mortar. The obtained mixture was put in a magnetic crucible and left to stand in an electrical furnace. The temperature of the electrical furnace was increased to 1300° C. to melt the mixture. The mixture was sufficiently homogenized, thereafter poured in water. Whereby, a block of fluoroaluminosilicate glass was obtained. The obtained glass block was pulverized for 20 hours by a ball mill, thereafter brought through a 120 mesh sieve. Whereby, a fluoroaluminosilicate glass powder was obtained. The composition of the obtained fluoroaluminosilicate glass powder was analyzed by fluorescent X-ray analysis. The analysis result is shown in Example 1 in Table 1.

Fluoroaluminosilicate glass powders of Examples 2 to 27 and Comparative Examples 1 to 8 were manufactured in the same way as the above.

<Manufacture of Powder for Dental Glass Ionomer Cement>

To 100 g of each fluoroaluminosilicate glass powder of Examples and Comparative Examples, 100 g of 1% aluminum phosphate aqueous solution was mixed to form a slurry. The obtained slurry was dried at 120° C. To the obtained material, polyacrylic acid powder (average molecular weight 30000) was further mixed to be 3 mass %, whereby a powder for dental glass ionomer cement was obtained.

<Manufacture of Dental Glass Ionomer Cement Hardened Body>

To 0.34 g of each powder for dental glass cement of Examples and Comparative Examples, 0.1 g of a commercially available glass ionomer cement sclerosing solution (product name: FUJI IX GP EXTRA (liquid), manufactured by GC CORPORATION) was added. The obtained material was mixed, whereby a dental glass ionomer cement hardened body was obtained.

<Acid Resistance Evaluation>

The acid resistance of the dental glass ionomer cement hardened body was evaluated based on the acid solubility test of JIS T6609-1. The dental glass ionomer cement composition after mixing was put in a mold made of polymethylmethacrylate having a hole of 5 mm in diameter and 2 mm in depth. The composition was welded by pressure via a film, and hardened. The obtained hardened body was left in a thermostatic bath at a temperature of 37° C. and a relative humidity of 100%, for 24 hours. After that, a surface of the cement hardened body with the mold still attached was polished with a water resistant polishing paper #1200, under water being poured, and smoothed. The initial thicknesses of the surface of the cement hardened body and the opposite surface were measured. This specimen was immersed in 0.1 mol/L of lactic acid/sodium lactate buffer solution (pH 2.74) at 37° C. for 24 hours. Thereafter, the thicknesses were measured in the same way, and the reduction was evaluated. The results are shown in Table 1.

<Measurement of Refractive Index $n_d$>

The refractive index $n_d$ of the fluoroaluminosilicate glass powder was measured as follows. The fluoroaluminosilicate glass powder was put in a test tube, to form a mixture solution of monomer having a refractive index lower than an expected refractive index. To the mixture solution, a mixture solution of monomer having a higher refractive index than the expected refractive index was adequately added and mixed. The obtained mixture liquid was observed under a sodium D line. The mixture solution having a ratio at which the refractive index of the mixture solution and the refractive index of the fluoroaluminosilicate glass powder were eventually conformed and the fluoroaluminosilicate glass powder became almost invisible was re-prepared. Further, several kinds of mixture solutions each having a different refractive index at a sodium D line by approximately 0.002 were prepared. Each of the several kinds of mixture solution was separately added in the test tube with the test powder in it and compared. Among them, the refractive index of the mixture solution that provided the highest transparency was measured by an Abbe refractometer, and the obtained refractive index was determined as the refractive index $n_d$ of the fluoroaluminosilicate glass powder. The measurement was carried out at 23° C. under 50% of relative humidity. The results are shown in Tables 1 to 3.

[Table 1]

TABLE 1

Unit of "Component": mass %

| Component | Component (converted) | Example 1 | Example 2 | Example 3 | Example 4 | Example 5 | Example 6 | Example 7 | Example 8 |
|---|---|---|---|---|---|---|---|---|---|
| Fluorine | F | 20.1 | 33.3 | 27.5 | 25.9 | 31.1 | 31.6 | 25.3 | 21.3 |
| Aluminum | $Al_2O_3$ | 23.7 | 18.0 | 22.0 | 25.6 | 18.0 | 18.0 | 22.0 | 25.6 |
| Silicon | $SiO_2$ | 22.8 | 19.5 | 20.0 | 19.2 | 19.0 | 19.5 | 20.0 | 19.2 |
| Sodium | $Na_2O$ | 3.0 | 2.7 | 2.2 | 2.7 | 2.6 | 2.7 | 2.4 | 3.0 |
| Potassium | $K_2O$ | 4.2 | 3.3 | 4.0 | 3.5 | 4.3 | 4.0 | 4.0 | 4.5 |
| Rare earth element or bismuth ($M_2O_3$) | $La_2O_3$ $Ce_2O_3$ $Y_2O_3$ $Yb_2O_3$ $Bi_2O_3$ | 4.2 | 3.0 | 3.1 | 2.9 | 3.8 | 4.0 | 2.0 | 3.5 |
| Other | $P_2O_5$ | 4.8 | 7.9 | 8.3 | 7.9 | 8.3 | 7.9 | 8.3 | 7.9 |
|  | SrO | 17.2 | 12.3 | 12.9 | 12.3 | 12.9 | 12.3 | 16.0 | 15.0 |
| $K_2O/Na_2O$ (mass ratio) |  | 1.43 | 1.22 | 1.82 | 1.27 | 1.65 | 1.48 | 1.67 | 1.50 |
| $M_2O_3/Na_2O$ (mass ratio) |  | 1.43 | 1.11 | 1.41 | 1.06 | 1.46 | 1.48 | 0.83 | 1.17 |
| Acid resistance [mm] |  | 86 | 83 | 80 | 86 | 84 | 80 | 88 | 84 |
| Refractive index |  | 1.458 | 1.463 | 1.464 | 1.464 | 1.463 | 1.458 | 1.470 | 1.466 |

Unit of "Component": mass %

| Component | Component (converted) | Example 9 | Example 10 | Example 11 | Example 12 | Example 13 | Example 14 |
|---|---|---|---|---|---|---|---|
| Fluorine | F | 18.5 | 26.5 | 18.9 | 18.3 | 13.0 | 40.1 |
| Aluminum | $Al_2O_3$ | 23.0 | 23.0 | 27.0 | 27.0 | 28.0 | 15.0 |
| Silicon | $SiO_2$ | 21.0 | 22.0 | 24.0 | 26.0 | 30.0 | 14.0 |
| Sodium | $Na_2O$ | 5.6 | 2.7 | 2.6 | 2.7 | 2.4 | 2.4 |
| Potassium | $K_2O$ | 8.0 | 4.1 | 4.3 | 4.0 | 4.0 | 4.3 |

TABLE 1-continued

| Component | Component (converted) | | | | | | |
|---|---|---|---|---|---|---|---|
| Rare earth element or bismuth ($M_2O_3$) | $La_2O_3$ | 0.6 | 1.5 | 2.0 | 1.8 | 1.4 | 3.0 |
| | $Ce_2O_3$ | | | | | | |
| | $Y_2O_3$ | | | | | | |
| | $Yb_2O_3$ | | | | | | |
| | $Bi_2O_3$ | | | | | | |
| Other | $P_2O_5$ | 8.3 | 7.9 | 8.3 | 7.9 | 8.3 | 8.3 |
| | SrO | 15.0 | 12.3 | 12.9 | 12.3 | 12.9 | 12.9 |
| $K_2O/Na_2O$ (mass ratio) | | 1.43 | 1.52 | 1.65 | 1.48 | 1.67 | 1.78 |
| $M_2O_3/Na_2O$ (mass ratio) | | 0.11 | 0.56 | 0.77 | 0.67 | 0.58 | 1.25 |
| Acid resistance [mm] | | 85 | 79 | 84 | 76 | 79 | 82 |
| Refractive index | | 1.456 | 1.469 | 1.467 | 1.476 | 1.478 | 1.457 |

[Table 2]

TABLE 2

Unit of "Component": mass %

| Component | Component (converted) | Example 15 | Example 16 | Example 17 | Example 18 | Example 19 | Example 20 | Example 21 |
|---|---|---|---|---|---|---|---|---|
| Fluorine | F | 12.9 | 28.4 | 24.2 | 24.3 | 20.7 | 24.4 | 21.0 |
| Aluminum | $Al_2O_3$ | 30.0 | 22.0 | 25.6 | 25.6 | 25.0 | 23.0 | 25.1 |
| Silicon | $SiO_2$ | 28.0 | 20.0 | 19.2 | 19.2 | 24.0 | 21.1 | 24.0 |
| Sodium | $Na_2O$ | 3.0 | 2.5 | 2.9 | 2.9 | 2.8 | 3.1 | 3.3 |
| Potassim | $K_2O$ | 4.5 | 3.9 | 4.4 | 4.3 | 4.3 | 5.0 | 5.0 |
| Rare earth element or bismuth ($M_2O_3$) | $La_2O_3$ | 1.4 | | | | | 5.4 | 6.4 |
| | $Ce_2O_3$ | | 2.0 | | | | | |
| | $Y_2O_3$ | | | 3.5 | | | | |
| | $Yb_2O_3$ | | | | | 2.0 | | |
| | $Bi_2O_3$ | | | | 3.5 | | | |
| Other | $P_2O_5$ | 7.9 | 8.3 | 7.9 | 7.9 | 8.3 | 5.0 | 3.0 |
| | SrO | 12.3 | 12.9 | 12.3 | 12.3 | 12.9 | 13.0 | 12.2 |
| $K_2O/Na_2O$ (mass ratio) | | 1.50 | 1.56 | 1.52 | 1.48 | 1.54 | 1.61 | 1.52 |
| $M2O3/Na_2O$ (mass ratio) | | 0.47 | 0.80 | 1.21 | 1.21 | 0.71 | 1.74 | 1.94 |
| Acid resistance [mm] | | 87 | 75 | 78 | 87 | 89 | 96 | 74 |
| Retractive index | | 1.469 | 1.469 | 1.466 | 1.469 | 1.468 | 1.485 | 1.491 |

Unit of "Component": mass %

| Component | Component (converted) | Example 22 | Example 23 | Example 24 | Example 25 | Example 26 | Example 27 |
|---|---|---|---|---|---|---|---|
| Fluorine | F | 22.1 | 14.8 | 21.4 | 22.0 | 17.8 | 23.4 |
| Aluminum | $Al_2O_3$ | 23.0 | 25.3 | 26.1 | 24.0 | 26.3 | 23.0 |
| Silicon | $SiO_2$ | 21.9 | 30.1 | 23.1 | 21.9 | 26.0 | 21.1 |
| Sodium | $Na_2O$ | 3.2 | 3.2 | 3.3 | 3.2 | 3.2 | 3.1 |
| Potassim | $K_2O$ | 5.1 | 4.9 | 5.0 | 5.1 | 4.9 | 5.0 |
| Rare earth element or bismuth ($M_2O_3$) | $La_2O_3$ | 8.4 | | | | | 5.4 |
| | $Ce_2O_3$ | | 9.7 | | | | |
| | $Y_2O_3$ | | | 7.0 | | | |
| | $Yb_2O_3$ | | | | 8.4 | | |
| | $Bi_2O_3$ | | | | | 6.7 | |
| Other | $P_2O_5$ | 5.3 | 2.0 | 1.9 | 4.4 | 5.1 | 6.0 |
| | SrO | 11.0 | 10.0 | 12.2 | 11.0 | 10.0 | 13.0 |
| $K_2O/Na_2O$ (mass ratio) | | 1.59 | 1.53 | 1.52 | 1.59 | 1.53 | 1.61 |
| $M2O3/Na_2O$ (mass ratio) | | 2.63 | 3.03 | 2.12 | 2.63 | 2.09 | 1.74 |
| Acid resistance [mm] | | 75 | 90 | 74 | 75 | 90 | 96 |
| Retractive index | | 1.496 | 1.503 | 1.494 | 1.496 | 1.487 | 1.485 |

[Table 3]

TABLE 3

Unit of "Component": mass %

| Component | Component (converted) | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|
| Fluorine | F | 33.3 | 31.7 | 24.8 | 25.4 | 23.3 | 22.8 | 21.9 | 11.4 |
| Aluminum | $Al_2O_3$ | 18.0 | 23.2 | 28.0 | 26.5 | 26.5 | 26.5 | 25.0 | 25.6 |
| Silicon | $SiO_2$ | 26.0 | 20.0 | 24.0 | 25.2 | 26.0 | 23.0 | 24.0 | 25.0 |
| Sodium | $Na_2O$ | 6.0 | 5.0 | 3.0 | 3.0 | 3.0 | 5.7 | 3.6 | 3.0 |
| Potassium | $K_2O$ | | 1.0 | 2.0 | 5.8 | 6.0 | 5.8 | 4.0 | 6.0 |

TABLE 3-continued

Unit of "Component": mass %

| Component | Component (converted) | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|
| Rare earth element or bismuth ($M_2O_3$) | $La_2O_3$ |  |  |  |  | 1.1 |  | 1.0 | 1.1 |
|  | $Ce_2O_3$ |  |  |  |  |  |  |  |  |
|  | $Y_2O_3$ |  |  |  |  |  |  |  |  |
|  | $Yb_2O_3$ |  |  |  |  |  |  |  |  |
|  | $Bi_2O_3$ |  |  |  |  |  |  |  |  |
| Other | $P_2O_5$ | 4.7 | 4.1 | 4.2 | 3.0 | 2.0 | 3.2 | 4.5 | 2.9 |
|  | SrO | 12.0 | 15.0 | 14.0 | 11.1 | 12.1 | 13.0 | 16.0 | 25.0 |
| $K_2O/Na_2O$ (mass ratio) |  | 0.00 | 0.20 | 0.67 | 1.93 | 2.00 | 1.02 | 1.11 | 2.00 |
| $M_2O_3/Na_2O$ (mass ratio) |  | 0.00 | 0.00 | 0.00 | 0.00 | 0.37 | 0.00 | 0.28 | 0.37 |
| Acid resistance [mm] |  | 160 | 158 | 130 | 109 | 149 | 132 | 130 | 40 |
| Refractive index |  | 1.448 | 1.463 | 1.462 | 1.457 | 1.467 | 1.472 | 1.481 | 1.522 |

The invention claimed is:

1. A fluoroaluminosilicate glass powder wherein a mass ratio of potassium to sodium in component is in the range of from 1.2 to 1.9 in terms of oxide, and the content of fluorine in the component is 13 mass % to 40 mass %.

2. The fluoroaluminosilicate glass powder according to claim 1, further comprising a rare earth element or bismuth, wherein a mass ratio of the rare earth element or bismuth to the sodium in the fluoroaluminosilicate glass powder is in the range of from 0.1 to 1.5 in terms of oxide.

3. The fluoroaluminosilicate glass powder according to claim 1 having a refractive index $n_d$ of in the range of from 1.42 to 1.47.

4. A dental glass ionomer cement composition comprising the fluoroaluminosilicate glass powder according to claim 1.

5. The fluoroaluminosilicate glass powder according to claim 2 having a refractive index $n_d$ of in the range of from 1.42 to 1.47.

6. A dental glass ionomer cement composition comprising the fluoroaluminosilicate glass powder according claim 2.

7. A dental glass ionomer cement composition comprising the fluoroaluminosilicate glass powder according claim 3.

8. A dental glass ionomer cement composition comprising the fluoroaluminosilicate glass powder according claim 5.

9. A fluoroaluminosilicate glass powder wherein a mass ratio of potassium to sodium in component is in the range of from 1.2 to 1.9 in terms of oxide, and the content of silicon in the component is 15 mass % to 30 mass % in terms of oxide.

10. The fluoroaluminosilicate glass powder according to claim 9, further comprising a rare earth element or bismuth, wherein a mass ratio of the rare earth element or bismuth to the sodium in the fluoroaluminosilicate glass power is in the range of from 0.1 to 1.5 in terms of oxide.

11. The fluoroaluminosilicate glass powder according to claim 9 having a refractive index $n_d$ of in the range of from 1.42 to 1.47.

12. A dental glass ionomer cement composition comprising the fluoroaluminosilicate glass powder according claim 9.

* * * * *